United States Patent [19]

Motegi et al.

[11] Patent Number: 4,878,942

[45] Date of Patent: Nov. 7, 1989

[54] BENZAMIDE DERIVATIVE, PROCESS FOR ITS PRODUCTION AND PLANT GROWTH REGULANT

[75] Inventors: Takeo Motegi; Mitsumasa Yamazaki; Hiroyuki Iguchi; Kaoru Kasahara, all of Tokyo, Japan

[73] Assignee: Hodogaya Chemical Co., Ltd., Tokyo, Japan

[21] Appl. No.: 222,256

[22] Filed: Jul. 21, 1988

[30] Foreign Application Priority Data

Jul. 23, 1987 [JP] Japan .................................. 62-182369

[51] Int. Cl.$^4$ ............................................ A01N 37/38
[52] U.S. Cl. ........................................ 71/109; 71/116; 71/118; 560/45; 562/455; 564/156
[58] Field of Search ........................... 560/45; 562/455; 564/156; 260/501.11; 71/109, 116, 118

[56] References Cited

U.S. PATENT DOCUMENTS 3,549,689 12/1970 Frey et al. ............................ 562/455
4,739,101 4/1988 Bourgogne et al. .................. 560/45

FOREIGN PATENT DOCUMENTS 0291245 11/1988 European Pat. Off. ............ 562/455
436936  3/1968 Japan .................................... 562/455
1077936  8/1967 United Kingdom ................ 562/455

Primary Examiner—Bruce Gray
Attorney, Agent, or Firm—Oblon, Spivak, McClelland, Maier & Neustadt

[57] ABSTRACT

A benzamide derivative of the formula:

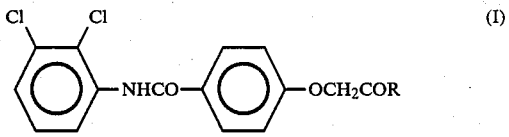

wherein R is hydroxyl, alkoxy, alkoxyalkoxy, alkoxyalkoxyalkoxy, alkenylalkoxy, alkenylalkoxyalkoxy, alkynylalkoxy, alkynylalkoxyalkoxy, monoalkylamino, dialkylamino or O-cat wherein cat is an inorganic or organic cation.

4 Claims, No Drawings

BENZAMIDE DERIVATIVE, PROCESS FOR ITS PRODUCTION AND PLANT GROWTH REGULANT

The present invention relates to a benzamide derivative, a process for its production and a plant growth regulant containing it.

In the case of rice or wheat, it happens not infrequently that the crop plants are lodged by wind or rain immediately before the harvest time, whereby the yield drops substantially. There have been proposed some chemical compounds which are intended to regulate the stems to be short and strong against such lodging force. However, there have been problems such that an attempt to control the stems to make them sufficiently strong, is likely to adversely affect the panicles, or the effectiveness of such treatment is very much influenced by the weather, the growing state or the timing or season for the treatment.

In the case of a lawn or hedge trees, or grass in a non-agricultural field, even if such plants are neatly trimmed or mown, they tend to grow quickly again. There have been some drugs tested for effectivemess so that cutting or mowning may be thereby ommitted. However, a satisfactory compound has not yet been available.

In the case of fruit trees, a thinning agent is frequently used to prevent the fruit trees from bearing so many fruits that the fruits tend to be small in size. However, the range of application is very narrow, and the method for its use is very difficult.

On the other hand, it is also an important area to increase the number of flowers or fruits.

In the case of root-crops, the quality of the root degrades when flower stalk develops. Therefore, a compound to control the development of the flower stalk is desired.

In the case of sugar cane, it has been attempted to increase the yield by preventing the heading or by increasing the sugar content by some physiological action.

Further, in the case of potatoes or onions, it is important to delay the sprout during their storage.

The above instances are merely exemplary, and there may be many other areas where the growth of plants is desired to be controlled. In each area, there may be some compounds which are actually used. However, there has been no compound which is fully satisfactory. It is therefore desired to develop an improved compound.

The present inventors have conducted extensive research on the herbicidal and plant growth regulating activities of various compounds and have found that certain benzamide derivatives exhibit various interesting activities including herbicidal activities against various plants, activities to shorten stems, to promote tillering, to control development of fresh buds or in some cases to promote development of axillary buds. On the basis of this discovery, a furhter study has been made, and as a result, the present invention has been accomplished.

The present invention provides a benzamide derivative of the formula:

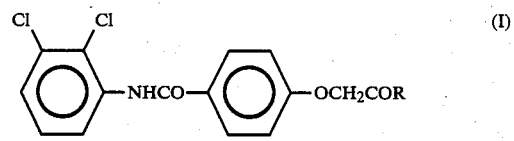
(I)

wherein R is hydroxyl, alkoxy, alkoxyalkoxy, alkoxyalkoxyalkoxy, alkenylalkoxy, alkenylalkoxyalkoxy, alkynylalkoxy, alkynylalkoxyalkoxy, monoalkylamino, dialkylamino or O-cat wherein cat is an inorganic or organic cation.

The present invention also provides a plant growth regulant comprising an effective amount of a benzamide derivative of the formula I and a carrier, and use of a compound of the formula I as a plant growth regulant.

Further, the present invention provides a process for producing a benzamide derivative of the formula I, which comprises reacting 4-hydroxy-N-(2,3-dichlorophenyl)-benzamide with a compound of the formula $XCH_2COR$ wherein R is as defined above and X is a halogen atom, or reacting 4-(2,3-diclorophenyl-carbamoyl)-phenoxyacetyl chloride with a compound of the formula RH wherein R is as defined above.

Now, the present invention will be described in detail with reference to the preferred embodiments.

In Table 1, representative compounds of the present invention are given. These compounds will be referred to hereinafter by the compound numbers identified in Table 1.

TABLE 1

| Compound No. | Chemical formula | Melting point (°C.) |
|---|---|---|
| 1 | Cl,Cl-C₆H₃-NHCO-C₆H₄-OCH₂COOH | 198–199.5 |
| 2 | Cl,Cl-C₆H₃-NHCO-C₆H₄-OCH₂COOC₂H₅ | 126–129 |
| 3 | Cl,Cl-C₆H₃-NHCO-C₆H₄-OCH₂COOC₃H₇—n | 131–135 |

TABLE 1-continued

| Compound No. | Chemical formula | Melting point (°C.) |
|---|---|---|
| 4 | 2,3-Cl₂-C₆H₃-NHCO-C₆H₄-OCH₂COOC₃H₇—i | 130–132 |
| 5 | 2,3-Cl₂-C₆H₃-NHCO-C₆H₄-OCH₂COOC₄H₉—n | 132–136 |
| 6 | 2,3-Cl₂-C₆H₃-NHCO-C₆H₄-OCH₂COOC₄H₉—iso | 114–118 |
| 7 | 2,3-Cl₂-C₆H₃-NHCO-C₆H₄-OCH₂COOC₄H₉—t | 149–150.5 |
| 8 | 2,3-Cl₂-C₆H₃-NHCO-C₆H₄-OCH₂COOC₆H₁₃—n | 158–161 |
| 9 | 2,3-Cl₂-C₆H₃-NHCO-C₆H₄-OCH₂COOC₁₂H₂₅—n | 153–158 |
| 10 | 2,3-Cl₂-C₆H₃-NHCO-C₆H₄-OCH₂COOCH₂—CH₂OC₄H₉—n | 87–92 |
| 11 | 2,3-Cl₂-C₆H₃-NHCO-C₆H₄-OCH₂COOCH₂CH₂—OCH₂CH₂OC₄H₉—n | 65–70 |
| 12 | 2,3-Cl₂-C₆H₃-NHCO-C₆H₄-OCH₂COOCH₂CH=CH₂ | 124–1127 |
| 13 | 2,3-Cl₂-C₆H₃-NHCO-C₆H₄-OCH₂COOCH₂CH=CHCH₂CH₃ | 135–139 |
| 14 | 2,3-Cl₂-C₆H₃-NHCO-C₆H₄-OCH₂COOCH₂C≡CH | 95–101 |

Note: Each compound has the structure: 2,3-dichlorophenyl–NHCO–phenyl–O–R, where R is the group shown.

TABLE 1-continued

| Compound No. | Chemical formula | Melting point (°C.) |
|---|---|---|
| 15 | 2,3-Cl₂-C₆H₃-NHCO-C₆H₄-OCH₂CONHCH₃ | 196–197.5 |
| 16 | 2,3-Cl₂-C₆H₃-NHCO-C₆H₄-OCH₂CONHC₂H₅ | 158–160.5 |
| 17 | 2,3-Cl₂-C₆H₃-NHCO-C₆H₄-OCH₂CONHC₃H₇—n | 170–171.5 |
| 18 | 2,3-Cl₂-C₆H₃-NHCO-C₆H₄-OCH₂CONHC₃H₇—i | 159–161.5 |
| 19 | 2,3-Cl₂-C₆H₃-NHCO-C₆H₄-OCH₂CONHC₄H₉—n | 141–142 |
| 20 | 2,3-Cl₂-C₆H₃-NHCO-C₆H₄-OCH₂CONHC₄H₉—iso | 170–171 |
| 21 | 2,3-Cl₂-C₆H₃-NHCO-C₆H₄-OCH₂CONHC₄H₉—t | 166–168.5 |
| 22 | 2,3-Cl₂-C₆H₃-NHCO-C₆H₄-OCH₂CONHC₁₂H₂₅—n | 129–131.5 |
| 23 | 2,3-Cl₂-C₆H₃-NHCO-C₆H₄-OCH₂CON(CH₃)₂ | 136–138 |
| 24 | 2,3-Cl₂-C₆H₃-NHCO-C₆H₄-OCH₂CON(C₂H₅)₂ | 145.5–147 |
| 25 | 2,3-Cl₂-C₆H₃-NHCO-C₆H₄-OCH₂CON(C₃H₇—n)₂ | 138–140.5 |

TABLE 1-continued

| Compound No. | Chemical formula | Melting point (°C.) |
|---|---|---|
| 26 | 2,3-Cl$_2$-C$_6$H$_3$-NHCO-C$_6$H$_4$-OCH$_2$CON(CH$_3$)(C$_4$H$_9$-n) | 128–130.5 |
| 27 | 2,3-Cl$_2$-C$_6$H$_3$-NHCO-C$_6$H$_4$-OCH$_2$CON(C$_4$H$_9$-n)$_2$ | 140.5–144 |
| 28 | 2,3-Cl$_2$-C$_6$H$_3$-NHCO-C$_6$H$_4$-OCH$_2$CON(C$_4$H$_9$-sec)$_2$ | 143.5–146 |
| 29 | 2,3-Cl$_2$-C$_6$H$_3$-NHCO-C$_6$H$_4$-OCH$_2$COONa | More than 230 |
| 30 | 2,3-Cl$_2$-C$_6$H$_3$-NHCO-C$_6$H$_4$-OCH$_2$COOH·N(C$_2$H$_5$)$_3$ | 153–157 (Decomp.) |
| 31 | 2,3-Cl$_2$-C$_6$H$_3$-NHCO-C$_6$H$_4$-OCH$_2$COOH·NH$_2$C$_3$H$_7$-i | 203–207 (Decomp.) |
| 32 | 2,3-Cl$_2$-C$_6$H$_3$-NHCO-C$_6$H$_4$-OCH$_2$COOH·NH$_2$C$_4$H$_9$-n | 150–154 (Decomp.) |

The benzamide derivatives of the present invention can readily be obtained in good yields by reacting 4-hydroxy-N-(2,3-dichlorophenyl)-benzamide with various esters or amides of a haloacetic acid, in an organic solvent such as acetone, toluene, dioxane or N,N-dimethylformamide in the presence of an inorganic base such as potassium carbonate or sodium carbonate or an organic base such as pyridine or triethylamine.

Otherwise, they can be obtained by reacting 4-hydroxy-N-(2,3-dichlorophenyl)-benzamide with a haloacetic acid, in an aqueous solution in the presence of an inorganic base such as sodium hydroxide or potassium hydroxide to obtain 4-(2,3-dichlorophenylcarbamoyl)-phenoxyacetic acid (Compound No. 1), reacting this compound with an inorganic halide such as thionyl chloride or an organic halide such as phosgene in an organic solvent such as dioxane or toluene to convert it to its acid chloride derivative, and then reacting this acid chloride derivative with various alcohols, alkoxyalcohols, alkoxyalkoxyalcohols, alkenylalcohols, alkenylalkoxyalcohols, alkynylalcohols, alkynylalkoxyalcohols, monoalkylamines or dialkylamines, in an aqueous solution or in an organic solvent such as acetone, toluene or dioxane in the presence of an inorganic base such as potassium carbonate or sodium carbonate or an organic base such as pyridine or triethylamine.

EXAMPLE 1

(Preparation of Compond No. 2 in Table 1)

28.2 g of 4-hydroxy-N-(2,3-dichlorophenyl)-benzamide, 20.0 g of ethyl bromoacetate and 20.7 g of potassium carbonate were dispersed in 150 ml of N,N-dimethylformamide, and the dispersion was stirred at a temperature of from 120° to 140° C. for 4 hours. After completion of the reaction, the reaction solution was poured into 500 ml of a 2% hydrochloric acid aqueous solution. The crude product obtained by collecting precipitates by filtration, was recrystallized from toluene to obtain 34.5 g of desired ethyl 4-(2,3-dichlorophenyl-carbamoyl)-phenoxyacetate. Yield: 93.4% Melting point: 126°–129° C.

EXAMPLE 2

(Preparation of Compound No. 1 in Table 1)

2.82 g of 4-hydroxy-N-(2,3-dichlorophenyl)-benzamide and 1.67 g of bromoacetic acid were dissolved in 10 ml of dioxane. To this solution, a mixture of 0.97 g of sodium hydroxide and 2 ml of water was dropwise added over a period of 10 minutes at a temperature of 20° C. under stirring. After the dropwise addition, the reaction solution was stirred at a temperature of 80° C. for 2 hours. After completion of the reaction, the reaction solution was poured into 50 ml of water, and acidified with hydrochloric acid. Then, the crude product obtained by collecting precipitates by filtration, was recrystallized from toluene/methanol to obtain 2.5 g of desired 4-(2,3-dichlorophenyl-carbamoyl)-phenoxyacetic acid. Yield: 70.6% Melting point: 198°-199.5° C.

EXAMPLE 3

(Preparation of Compound No. 5 in Table 1)

A mixture of 3.54 g of 4-(2,3-dichlorophenyl-carbamoyl)-phenoxyacetic acid, 3.57 g of thionyl chloride and 30 ml of dioxane was stirred at a temperature of 80° C. for 4 hours. An excess amount of thionyl chloride and dissolved hydrochloric acid gas, sulfurous acid gas and dioxane were distilled off by a rotary evaporator to obtain 4-(2,3-dichlorophenyl-carbamoyl)-phenoxyacetyl chloride as the residue after distillation.

On the other hand, 0.8 g of n-butanol and 2.0 g of triethylamine were dissolved in 20 ml of dioxane. To this solution, a solution prepared by dissolving above 4-(2,3-dichlorophenyl-carbamoyl)-phenoxyacetyl chloride in 5 ml of dioxane, was dropwise added over a period of 5 minutes at room temperature under stirring. After completion of the dropwise addition, the stirring was continued at room temperature for further 5 hours. After completion of the reaction, the reaction solution was poured into 200 ml of a 2% hydrochloric acid aqueous solution. The precipitates were collected by filtration, washed with a dilute alkaline aqueous solution and water, and dried. Then, the precipitates were recrystallized from toluene to obtain 3.3 g of n-butyl 4-(2,3-dichlorophenyl-carbamoyl)-phenoxyacetate. Yield: 80.5% as calculated on the basis of 4-(2,3-dichlorophenyl)carbamoylacetic acid) Melting point: 132°-136° C.

EXAMPLE 4

(Preparation of Compound No. 18 in Table 1)

0.71 g of isopropylamine and 3.0 g of triethylamine were dissolved in 20 ml of dioxane. To this solution, a solution prepared by dissolving 4-(2,3-dichlorophenyl-carbamoyl)-phenoxyacetyl chloride prepared in the same manner as in Example 3 in 5 ml of dioxane, was dropwise added over a period of about 5 minutes at room temperature under stirring. After completion of the dropwise addition, the stirring was continued at room temperature for further 5 hours. After completion of the reaction, the reaction solution was treated in the same manner as in Example 3 to obtain 3.8 g of desired N-isopropyl-4-(2,3-dichlorophenyl-carbamoyl)-phenoxyacetamide.

Yield: 92.5% as calculated on the basis of 4-(2,3-dichlorophenyl-carbamoyl)-phenoxyacetic acid)
Melting point: 159°-161.5° C.

EXAMPLE 5

(Preparation of Compound No. 30 in Table 1)

1.02 g of 4-(2,3-dichlorophenyl-carbamoyl)-phenoxyacetic acid was dissolved in 5 ml of methanol. To this solution, 0.33 g of triethylamine was dropwise added over a period of about 5 minutes at room temperature under stirring. Further, the stirring was continued at room temperature for 1 hour. Then, excess amounts of triethylamine and methanol were distilled off by a rotary evaporator to obtain 1.2 g of the desired triethylamine salt of 4-(2,3-dichlorophenyl-carbamoyl)-phenoxyacetic acid. Yield: 90.7% Melting point: 153°-157° C. (Decomposed)

The plant growth regulant of the present invention may be prepared in the form of e.g. a wettable powder, an emulsifiable concentrate, a liquid formulation, a granule, a dust, a flowable or an aqueous solution by mixing the active ingredient with various kinds of carriers depending upon its physicochemical properties.

Among such carriers, as liquid carriers, conventional organic solvents may be employed, and as solid carriers, conventional mineral powders may be employed. Further, during the preparation of such a formulation, a surface active agent may be added to impart emulsifiability, dispersibility and spreadability to the formulation. Further, the compound of the present invention may be, as the case requires, combined with a fertilizer, a herbicide, an insecticide or a fungicide in the form of a unitary formulation or as a tank mix for application.

As a carrier, an inert inorganic substance such as bentonite, clay, zeolite or talc may be used. As an organic solvent, a solvent in which various compounds are well soluble, such as xylene, toluene, cyclohexanone or a glycol may be employed. Further, as a dispersing agent, an emulsifying agent or a fixing agent, there may be employed an anionic or nonionic surface active agent such as lignin sulfonate, naphthalene sulfonate, dialkyl sulfosuccinate, polyoxyethylene nonyl phenyl ether, polyoxyethylene stearyl ether or polyoxyethylene dodecyl ether.

When the compound of the present invention is used as a herbicide, the active ingredient is applied in a sufficient amount to obtain desired herbicidal effects. The dose of the active ingredient is within a range of from 1 to 200 g/are, usually preferably from 5 to 50 g/are. It may be formulated into a formulation such as a wettable powder, an emulsifiable concentrate, a dust or a granule, which contains the active ingredient in an amount of from 0.1 to 80% by weight, preferably from 1 to 50% by weight.

When the compound of the present invention is used as a herbicide, it mainly controls the germination and growth of weeds to eventually kill the weeds. In a paddy field, the herbicide of the present invention exhibits excellent herbicidal effects against not only annual weeds such as barnyardgråss (*Echinochloa oryzicola*), but also perennial weeds such as sagittaria (*Sagittaria pygmaea*) and flat-sedge (*Cyperus microiria*). No substantial phytotoxicity to transplanted paddy rice plants has been observed. Also in soil treatment or foliar treatment in an upland field, it exhibits selective herbicidal effects for corn (*Zea mays*), soybean (*Glycine max*) or the like.

When the compound of the present invention is used as a plant growth regulant, it may be applied in a dose of the active ingredient within a range of from 0.1 to 100 g/are, usually preferably from 1 to 50 g/are depending upon the type of the crop plant, the type of the compound or the time of application. The active ingredient compound may be formulated into a formulation such as a wettble powder, an emulsifiable concentrate, a dust or a granule, which contains from 0.1 to 80% by weight, preferably from 1 to 50% by weight, of the active ingredient.

When the compound of the present invention is used as a plant growth regulant.

It is absorbed mainly from the foliage of plants, and then transferred in the plant body to exhibit its activities preferentially at the protion where the growth is most active. The exhibition of the activities varies depending upon the compound, the concentration, the type of plants or the growing stage of plants. However, it is assumed that the activities are antagonistic against auxin or gibberellin as the plant hormone.

As specific effects, in the case of gramineous plants, the shortening of the length between nodes is observed after the foliar treatment, and in some cases, tillering is facilitated. Further, with respect to broad leaf plants, the plant growth regulant of the present invention is effective to suppress the formation of new buds, to prevent spindly growth or to promote formation of axillary buds or flower buds.

Thus, the compound of the present invention has a wide range of applications, for example, as a lodging reducing agent, as an agent for reducing the necessity of trimming hedge, as an agent for shortening flower trees, grasses or large weeds, or as a thinning agent.

When the compound of the present invention is used as a plant growth regulant in foliar treatment, the dose may usually be smaller than that required for a herbicide. However, the dose varies depending upon the type of plants or the purpose of the use. For example, when it is used to reduce the lodging of plants, it may be applied in an amount of from 0.5 to 3 g/are in the case of rice and from 2 to 10 g/are in the case of wheats. When it is used to shorten plants, it may be used in an amount of from 3 to 15 g/are in the case of grasses such as Bermuda grass, from 10 to 40 g/are in the case of trees and from 20 to 50 g/are in the case of large weeds in a non-agricultural field. In some cases, it may be used in an amount outside the above ranges. Whereas, when it is used as a thinning agent or to induce flower buds, the dose may be at a level of from 0.1 to 1 g/are.

Now, the present invention will be described in further detail with reference to Formulation Examles and Test Examples.

FORMLATION EXAMPLE 1: Preparation of wettable powder

To 40 parts by weight of Compound No. 5, 52 parts by weight of kaolin clay and 3 parts by weigth of white carbon were added, and the mixture was mixed and pulverized by a kneader. Then, 4 parts of a powdery surfactant Sorpol* 5039 (* trade mark, Toho Kagaku K.K.) and 1 part by weight of a powdery surfactant Rapizol* BB-75 (* trade mark, Nippon Oil and Fats Co., Ltd.) were mixed to obtain a wettable powder containing 40% by weight of Compound No. 5.

FORMULATION EXAMPLE 2: Preparation of emulsifiable concentrate 15 parts by weight of Compound No. 10 was dissolved in 42 parts by weight of xylene and 33 parts by weight of cyclohexanone, and 10 parts by weight of Sorpol 800A was added thereto and dissolved under stirring to obtain an emulsifiable concentrate containing 15% by weight of Compound No. 10.

FORMULATION EXAMPLE 3: Preparation of dust 5 parts by weight of a wettable powder containing 40% by weight of Compound No. 15 prepared in the same manner as in Example 1 was thoroughly mixed with 0.3 part by weight of Rapizol BB-75 and 94.7 parts by weight of clay to obtain a dust containing 2% by weight of Compound No. 15.

FORMULATION EXAMPLE 4: Preparation of micro-granule formulation

To 50 parts by weight of Compound No. 1, 3 parts by weight of white carbon and 47 parts by weight of kaolin clay were mixed, and the mixture was pulverized. Two parts by weight of the pulverized mixture was added to 96 parts by weight of fine particulate zeolite under stirring in a speed kneader. While the stirring was continued, 2 parts by weight of polyoxyethylene dodecyl ether diluted with water was poured thereto. The mixture was prepared with a small amount of water until no powder was observed. The mixture was withdrawn and then, dried under air stream to obtain a micro-granule formulation containing 1% by weight of Compound No. 1.

FORMULATION EXAMPLE 5: Preparation of granule

To 50 parts by weight of Compound No. 3, 3 parts by weight of white carbon and 47 parts by weight of clay were added, and the mixture was pulverized by a kneader. Two parts by weight of the pulverized mixture, 40 parts by weight of bentonite, 43 parts by weight of clay, 5 parts by weight of sodium tripolyphosphate and 2 parts by weight of a powdery surfactant Rapizol* BB-75 (* trade mark, Nippon Oil and Fats Co., Ltd.) were charged into a kneader, and the mixture was thoroughly mixed. Then, water was added thereto, and the mixture was thoroughly kneaded, granulated by a granulator and dried under air stream to obtain granules containing 5% by weight of Compound No. 3.

TEST EXAMPLE 1

A 400 cm$^2$ pot was filled with a paddy field soil. Seeds of barnyardgrass (*Echinochloa oryzicola*), monochoria (*Monochoria vaginalis*) and bulrush (*Scirpus juncoides*) were uniformly sown in the soil surface layer and tubers of sagittaria (*Sagittaria pygmaea*) and cyperus (*Cyperus serotinus*) were planted. Water was introduced to a depth of 3 cm. Furhter, two paddy rice seedlings of 2-leaf stage were transplanted. Then, a diluted solution of a wettable powder of each test compound was dropwise applied in a predetermined amount of each compound. On the 20th day after the application, the herbicidal effects against the weeds and the response of the transplanted paddy rice plants to the test compound were evaluated. The results are shown in Table 2.

The evaluation was made in accordance with the following standards.

Herbicidal effect

0: Same as no treatment
1: 20% control
2: 40% control
3: 60% control
4: 80% control 5: Completely withered Phytotoxicity to crop plants —: No phytotoxicity
±: Slight phtotoxicity
+: Minor phytotoxicity
++: Medium phytotoxicity
+++: Serious phytotoxicity
(These standards will be used for evaluation hereinafter.)

squarters (*Chenopodium album*) and large crabgrass (*Digitaria sanguinalis*) were mixed with the surface soil, and seeds of wheat (*Triticum aestivum*), corn (*Zea mays*) and soybean (*Glycine max*) were sown in a depth of 3 cm.

After sowing, a diluted solution of each test compound was sprayed on the surface of the soil in a predetermined amont of the compound. On the 30th day after the treatment, the herbicidal effects against the weeds and the responses of the crop plants to each test herbi-

TABLE 2

| Compound No. | Formulation | Dose of the active ingredient (g/10a) | Phytotoxicity to paddy rice | Herbicidal effect | | | | |
|---|---|---|---|---|---|---|---|---|
| | | | | BAR* | MON* | BUL* | SAG* | CYP* |
| 1 | 40% wettable powder | 200 | + | 4.5 | 5 | 4 | 4 | 4.5 |
| | | 100 | — | 4 | 4 | 3 | 4 | 4 |
| | | 50 | — | 3.5 | 3.5 | 2 | 2 | 3.5 |
| 2 | " | 200 | + | 5 | 5 | 4 | 4 | 4.5 |
| | | 100 | — | 4 | 4 | 3 | 4 | 4 |
| | | 50 | — | 3.5 | 3.5 | 2.5 | 3 | 3.5 |
| 3 | " | 200 | — | 5 | 5 | 5 | 5 | 5 |
| | | 100 | — | 5 | 5 | 4.5 | 4.5 | 4.5 |
| | | 50 | — | 4.5 | 4 | 3 | 4 | 4 |
| 7 | 20% wettable powder | 200 | + | 5 | 5 | 4 | 4.5 | 5 |
| | | 100 | — | 4 | 4 | 4 | 4 | 4 |
| | | 50 | — | 3 | 3 | 3 | 2 | 3 |
| 10 | 15% emulsifiable concentrate | 200 | — | 5 | 4.5 | 4 | 4.5 | 5 |
| | | 100 | — | 5 | 4 | 4 | 4 | 4.5 |
| | | 50 | — | 4.5 | 3 | 3 | 3 | 3 |
| 12 | 20% wettable powder | 200 | + | 5 | 5 | 4.5 | 5 | 5 |
| | | 100 | — | 4 | 4.5 | 4 | 4 | 4 |
| | | 50 | — | 3 | 4 | 3 | 3 | 2 |
| 14 | " | 200 | — | 5 | 4 | 4 | 4 | 4.5 |
| | | 100 | — | 4 | 4 | 3 | 4 | 4 |
| | | 50 | — | 3 | 3.5 | 3 | 2 | 3 |
| 16 | 40% wettable powder | 200 | + | 5 | 5 | 4.5 | 4.5 | 4 |
| | | 100 | — | 4 | 3.5 | 4 | 4 | 4 |
| | | 50 | — | 4 | 3 | 3 | 3 | 3.5 |
| 20 | " | 200 | + | 5 | 5 | 5 | 5 | 5 |
| | | 100 | — | 5 | 5 | 4.5 | 4.5 | 4.5 |
| | | 50 | — | 4.5 | 4.5 | 3 | 3.5 | 3 |
| 22 | " | 200 | — | 5 | 5 | 5 | 5 | 5 |
| | | 100 | — | 4.5 | 4 | 4 | 4.5 | 4.5 |
| | | 50 | — | 4 | 4 | 3 | 3 | 2 |
| 28 | 40% wettable powder | 200 | — | 5 | 5 | 5 | 5 | 5 |
| | | 100 | — | 5 | 5 | 5 | 4.5 | 4.5 |
| | | 50 | — | 5 | 5 | 4 | 4 | 4 |
| 29 | Aqueous solution | 200 | + | 5 | 5 | 4.5 | 4 | 4.5 |
| | | 100 | — | 4 | 4.5 | 4 | 3 | 4 |
| | | 50 | — | 3 | 4 | 3 | 2 | 3 |
| 31 | 40% wettable powder | 200 | — | 5 | 5 | 5 | 5 | 5 |
| | | 100 | — | 4.5 | 5 | 4 | 4 | 4 |
| | | 50 | — | 4 | 4 | 3 | 2 | 3 |
| 3 | 5% granule | 200 | — | 5 | 5 | 5 | 5 | 5 |
| | | 100 | — | 5 | 5 | 4 | 4.5 | 4.5 |
| | | 50 | — | 4.5 | 3.5 | 3 | 3.5 | 3 |
| 20 | " | 200 | — | 5 | 5 | 5 | 5 | 5 |
| | | 100 | — | 5 | 4.5 | 4.5 | 4 | 4.5 |
| | | 50 | — | 4 | 4 | 3 | 3 | 3 |
| 28 | 5% granule | 200 | — | 5 | 5 | 5 | 5 | 5 |
| | | 100 | — | 5 | 5 | 4.5 | 4.5 | 4.5 |
| | | 50 | — | 4.5 | 4.5 | 4 | 3 | 3 |

Note:
*BAR: barnyardgrass (*Echinochloa oryzicola*)
MON: monochoria (*Monochoria vaginalis*)
BUL: bulrush (*Seirpus juncoides*)
SAG: sagittaria (*Sagittaria pygmaea*)
CYP: cyperus (*Cyperus serotinus*)

TEST EXAMPLE 2: Upland soil treatment test

A 400 cm² pot was filled with an upland soil, and seeds of slender amaranth (*Amaranthus viridis*), lambcide were evaluated by the same standards as in Test Example 1. The results are shown in Table 3.

TABLE 3

| Compound No. | Dose of the active ingredient (g/10a) | Phytotoxicity to crop plants | | | Herbicidal effect | | |
|---|---|---|---|---|---|---|---|
| | | WHE* | COR* | SOY* | SLE* | LAM* | LAR* |
| 1 | 500 | — | — | + | 5 | 5 | 5 |
| | 250 | — | — | — | 4.5 | 4 | 4 |
| | 125 | — | — | — | 4 | 4 | 3.5 |
| 2 | 500 | + | — | + | 5 | 5 | 5 |
| | 250 | — | — | — | 5 | 5 | 4.5 |
| | 125 | — | — | — | 4 | 4 | 3 |
| 4 | 500 | — | — | + | 5 | 5 | 5 |
| | 250 | — | — | — | 5 | 5 | 5 |
| | 125 | — | — | — | 4.5 | 4 | 4 |
| 10 | 500 | — | — | — | 5 | 5 | 4 |
| | 250 | — | — | — | 4 | 4 | 4 |
| | 125 | — | — | — | 3 | 3.5 | 3.5 |
| 15 | 500 | + | — | — | 5 | 5 | 5 |
| | 250 | — | — | — | 5 | 5 | 5 |
| | 125 | — | — | — | 5 | 4.5 | 4 |
| 17 | 500 | + | — | + | 5 | 5 | 5 |
| | 250 | — | — | — | 4.5 | 5 | 5 |
| | 125 | — | — | — | 4.5 | 4 | 4 |
| 22 | 500 | — | — | + | 5 | 5 | 4 |
| | 250 | — | — | — | 4 | 4 | 4 |
| | 125 | — | — | — | 4 | 3 | 3.5 |
| 23 | 500 | — | — | — | 5 | 5 | 5 |
| | 250 | — | — | — | 5 | 5 | 5 |
| | 125 | — | — | — | 4.5 | 4.5 | 4 |
| 29 | 500 | — | — | — | 5 | 5 | 4.5 |
| | 250 | — | — | — | 4.5 | 4 | 3 |
| | 125 | — | — | — | 3 | 3 | 2 |
| 30 | 500 | — | — | — | 4.5 | 4.5 | 4 |
| | 250 | — | — | — | 4 | 4 | 4 |
| | 125 | — | — | — | 3.5 | 3 | 3 |

Note:
*WHE: wheat (*Triticum aestivum*)
COR: corn (*Zea mays*)
SOY: soybean (*Glycine max*)
SLE: slender amaranth (*Amaranthus viridis*)
LAM: lambsquarters (*Chenopodium album*)
LAR: large crabgrass (*Digitaria sanguinalis*)

TEST EXAMPLE 3

Foliar treatment tests on various plants (plant growth regulant)

Rice (*Oryza sativa*), barley (*Hordeum vulgare*), French bean (*Phaseolus vulgaris L.*) and lettuce were separately grown in porous pots of 60 cm², and thinned depending upon the size of the plants. The growth degrees were adjusted to a level of from 2 to 3 leaf stage, and a diluted solution of each test compound was applied in an amount of 10 liter/a to the foliage part of the plant by a spray gum. On the 30th day after the treatment, the growth inhibition was evaluated. The results are shown in Table 4.

The evaluation was made in accordance with the following standards:

Growth inhibition in height

0: Same as no treatment
1: Growth inhibition of about 20% as compared with no treatment
2: Growth inhibition of about 40% as compared with no treatment
3: Growth inhibition of about 60% as compared with no treatment
4: Growth inhibition of about 80% as compared with no treatment
5: No progress in growth observed since the treatment Effects of the treatment G: Green deepening
T: Tillering
M: Malformed leaves
B: Burning of leaves

TABLE 4

| Compound No. | Concentration (%) | Test plants Response value | | | |
|---|---|---|---|---|---|
| | | RI* | BA* | FR* | LE* |
| 1 | 0.1 | 5 | 5 | 4.5MB | 5 |
| | 0.05 | 4T | 5T | 4 | 5 |
| | 0.025 | 3 | 4 | 4 | 4 |
| 2 | 0.1 | 5 | 4T | 5B | 5 |
| | 0.05 | 4T | 3 | 5 | 5 |
| | 0.025 | 3.5 | 3 | 4 | 4 |
| 4 | 0.1 | 4.5T | 4T | 4.5MB | 5 |
| | 0.05 | 4.5T | 4T | 4.5M | 5 |
| | 0.025 | 4 | 3.5 | 4 | 4.5 |
| 5 | 0.1 | 5 | 4T | 4.5M | 4 |
| | 0.05 | 5 | 4 | 4 | 4 |
| | 0.025 | 4T | 3 | 3.5 | 3 |
| 7 | 0.1 | 4T | 3 | 4 | 4 |
| | 0.05 | 3 | 3 | 3 | 3 |
| | 0.025 | 2 | 2 | 2 | 2 |
| 8 | 0.1 | 4 | 3 | 4 | 4 |
| | 0.05 | 3 | 2 | 4 | 3.5 |
| | 0.025 | 2 | 1.5 | 3 | 2 |
| 10 | 0.1 | 4T | 4.5T | 5MB | 5 |
| | 0.05 | 4T | 4T | 4.5M | 5 |
| | 0.025 | 3.5 | 3.5 | 4 | 4.5 |
| 12 | 0.1 | 4.5T | 4T | 5MB | 4 |
| | 0.05 | 4.5T | 4 | 4.5 | 4 |
| | 0.025 | 4 | 3.5 | 4 | 3.5 |
| 13 | 0.1 | 4 | 3 | 4 | 4 |
| | 0.05 | 3 | 3 | 3 | 3.5 |

TABLE 4-continued

| Compound No. | Concentration (%) | Test plants Response value | | | |
|---|---|---|---|---|---|
| | | RI* | BA* | FR* | LE* |
| | 0.025 | 2 | 2 | 2 | 2.5 |
| 14 | 0.1 | 4T | 4T | 4 | 3 |
| | 0.05 | 4 | 4 | 3.5 | 3 |
| | 0.025 | 3 | 3 | 3 | 2 |
| 15 | 0.1 | 5 | 5 | 5MB | 5 |
| | 0.05 | 4.5T | 4T | 4.5M | 5 |
| | 0.025 | 3.5 | 3 | 4 | 4 |
| 17 | 0.1 | 5 | 4T | 5MB | 5 |
| | 0.05 | 4.5T | 4T | 4.5 | 5 |
| | 0.025 | 4T | 3.5 | 4 | 4 |
| 19 | 0.1 | 5 | 4T | 4 | 4 |
| | 0.05 | 5 | 4 | 4 | 4 |
| | 0.025 | 4T | 3.5 | 3 | 3.5 |
| 23 | 0.1 | 5T | 4 | 5MB | 5 |
| | 0.05 | 5T | 4 | 4.5 | 5 |
| | 0.025 | 4 | 3.5 | 4 | 4.5 |
| 25 | 0.1 | 3 | 3 | 3 | 3 |
| | 0.05 | 3 | 2.5 | 3 | 2 |
| | 0.025 | 2 | 2 | 2 | 1.5 |
| 29 | 0.1 | 5T | 5T | 5MB | 4 |
| | 0.05 | 4 | 4 | 4 | 4 |
| | 0.025 | 3 | 4 | 4 | 4 |
| 30 | 0.1 | 5 | 5 | 5MB | 4 |
| | 0.05 | 4T | 4.5 | 4.5 | 4 |
| | 0.025 | 3.5 | 4 | 4 | 3.5 |

Note:
*RI: Rice
BA: Barley
FR: French bean
LE: Lettuce

TEST EXAMPLE 4: Foliar treatment test on azelea

A diluted solution of each tested compound was applied to azelea (*Rhododendron indicum*) nursery stocks (height: 25-30 cm) grown in a porous pot of 200 cm$^2$ so that the entire nursely stocks were adequately wet (25 liter/a). Seven days later, they were trimmed, and 2 months later, the evaluation was conducted by the same standards as in Test Example 3. The results are shown in Table 5.

TABLE 5

| | Foliar treatment test on azelea | | |
|---|---|---|---|
| Compound No. | Concentration (%) | Growth inhibition | Other response |
| 1 | 0.1 | 4 | G |
| | 0.05 | 3 | |
| 2 | 0.1 | 5 | GB |
| | 0.05 | 4 | |
| 5 | 0.1 | 4 | M |
| | 0.05 | 3 | |
| 10 | 0.1 | 4.5 | G |
| | 0.05 | 4 | |
| 15 | 0.1 | 4 | |
| | 0.05 | 3.5 | |
| 24 | 0.1 | 4 | G |
| | 0.05 | 3 | |
| 29 | 0.1 | 4 | M |
| | 0.05 | 3 | |
| 30 | 0.1 | 3.5 | |
| | 0.05 | 3 | |

TEST EXAMPLE 5: Foliar treatment test on wheat

A field of wheat (Norin No. 61) sown in rows in early Nov., was divided into unit plots of 5 m×2 m. Each compound diluted to a predetermined concentration was sprayed over the entire surface in a unit plot in an amount corresponding to 10 liter/a by means of a hand sprayed on 14 days prior to heading i.e. late Apr. The dust and micro-granule formulation were applied manually.

In middle June, the stem length, the panicle length and the number of panicle and the grain weight per unit area were examined with respect to 50 stems which showed average growth. The lodging degree was moderate at the non-treated plots, and the plots where the lodging reducing effect was distinctly observed was marked with O. The results are shown in Table 5.

The numeral values represent percentage values relative to the non-treated area, and the values in the brackets ( ) are actually measured values.

TABLE 6

| | Foliar treatment test on wheat | | | | | |
|---|---|---|---|---|---|---|
| Compound No. | Applied amount (g/are) | Stem length (%) | Panicle length (%) | Number of panicles per m$^2$ | Grain weight (%) | Lodging Reducing effect |
| 1 | 10 | 76 | 92 | 90 | 95 | 0 |
| | 5 | 83 | 95 | 93 | 103 | 0 |
| | 2 | 92 | 99 | 95 | 104 | |
| 2 | 10 | 84 | 96 | 96 | 99 | 0 |
| | 5 | 88 | 102 | 101 | 104 | 0 |
| | 2 | 97 | 105 | 99 | 101 | |
| 15 | 10 | 80 | 95 | 95 | 94 | 0 |
| | 5 | 83 | 104 | 95 | 100 | 0 |
| | 2 | 90 | 101 | 101 | 103 | |
| 29 | 10 | 85 | 93 | 98 | 102 | 0 |
| | 5 | 90 | 105 | 102 | 101 | |
| | 2 | 102 | 104 | 100 | 99 | |
| 30 | 10 | 86 | 98 | 103 | 105 | 0 |
| | 5 | 92 | 104 | 101 | 103 | |
| | 2 | 96 | 98 | 104 | 103 | |
| 2% dust of compound No. 15 | 10 | 82 | 97 | 100 | 96 | 0 |
| | 5 | 85 | 100 | 98 | 100 | 0 |
| | 2 | 93 | 102 | 105 | 101 | |
| 1% micro-granule of compound No. 1 | 10 | 87 | 100 | 101 | 102 | 0 |
| | 5 | 93 | 98 | 102 | 104 | |
| | 2 | 100 | 101 | 99 | 102 | |
| Non-treatment | — | 100 (95 cm) | 100 (8.5 cm) | 100 (450 /m$^2$) | 100 (450 g /m$^2$) | |

TEST EXAMPLE 6: Foliar treatment test on Bermuda grass

Bermuda grass (T-328 variety) was divided into plots of 1 m×1 m. Five days after mowing, a diluted solution of each compound was uniformly applied in an amount corresponding to 10 liter/a to each plot by means of a hand sprayer. Ten days and 20 days after the application, the evaluation was conducted by the same evaluation standards as used in Test Example 3.

The change in the color of leaves was evaluated under the following standards:

| Color of leaves | | |
|---|---|---|
| Browning | Slight | B-1 |
| | Little | B-2 |
| | Substantial | B-3 |
| Green deeping | Slight | G-1 |
| | Little | G-2 |
| | Substantial | G-3 |

The results are shown in Table 7.

TABLE 7

Growth inhibition on foliar treatment test on Bermuda grass

| Compound No | Active ingredient (g/a) | 10 days later Inhibition | 10 days later Color of leaves | 20 days later Inhibition | 20 days later Color of leaves |
|---|---|---|---|---|---|
| 1 | 10 | 5 | G-1 | 5 | G-1 |
|  | 5 | 5 |  | 4.5 |  |
|  | 2.5 | 4 |  | 3 |  |
| 2 | 10 | 5 |  | 5 | G-1 |
|  | 5 | 4.5 |  | 4 |  |
|  | 2.5 | 4 |  | 3 |  |
| 6 | 10 | 5 |  | 5 |  |
|  | 5 | 4.5 |  | 4 |  |
|  | 2.5 | 4 |  | 3 |  |
| 9 | 10 | 5 |  | 4.5 |  |
|  | 5 | 4.5 |  | 3 |  |
|  | 2.5 | 4 |  | 2 |  |
| 10 | 10 | 5 | G-2 | 5 | G-1 |
|  | 5 | 5 | G-1 | 4.5 |  |
|  | 2.5 | 4 |  | 3 |  |
| 11 | 10 | 5 | G-1 | 5 | G-1 |
|  | 5 | 5 |  | 4 |  |
|  | 2.5 | 4 |  | 3 |  |
| 18 | 10 | 5 |  | 4.5 |  |
|  | 5 | 4 |  | 3 |  |
|  | 2.5 | 3.5 |  | 2 |  |
| 21 | 10 | 5 | B-1 | 4.5 |  |
|  | 5 | 4.5 |  | 3 |  |
|  | 2.5 | 3 |  | 2 |  |
| 26 | 10 | 5 | B-1 | 4.5 |  |
|  | 5 | 4.5 |  | 3 |  |
|  | 2.5 | 2 |  | 1 |  |
| 27 | 10 | 5 | B-2 | 4.5 | B-1 |
|  | 5 | 4 | B-1 | 3 |  |
|  | 2.5 | 2 |  | 1 |  |
| 29 | 10 | 5 | G-1 | 5 | G-1 |
|  | 5 | 5 |  | 4 |  |
|  | 2.5 | 4.5 |  | 2 |  |
| 32 | 10 | 5 | G-1 | 4.5 |  |
|  | 5 | 5 |  | 3 |  |
|  | 2.5 | 4 |  | 2 |  |

TEST EXAMPLE 7

Foliar treatment test on paddy field rice

A paddy field to which paddy field rice seedlings (Koshihikari) were transplanted by a transplanter, was divided into unit plots of 6 rows ×3 m. Each regulant diluted with water to a predetermined concentration was uniformly sprayed in an amount corresponding to 10 liter/a by a sprayer on 7 days prior to heading (A fixing agent was added to a wettable powder and an aqueous solution.) After the harvest, the stem length, the panicle length and the panicle weight were measured with respect to 20 plants. The results are shown in Table 8.

The numerical values represent percentage values relative to the non-treated plots, and were rounded off to decimal place. Further, the lodging degree as observed was represented with a 5-step evaluation using 0 to 4. Further, with respect to the representative plot, the length between nodes was measured. The results are shown in Table 9.

TABLE 8

Foliar treatment test on rice

| Compound No. | g/are (A.I) | Stem length | Panicle length | Panicle weight | Lodging reducing effect | Plot No. |
|---|---|---|---|---|---|---|
| 1 | 1 | 81 | 100 | 98 | 0 | 1 |
|  | 0.5 | 88 | 102 | 106 | 1 | 2 |
|  | 0.25 | 98 | 105 | 103 | 2 | 3 |
| 2 | 1 | 87 | 101 | 106 | 0 | 4 |
|  | 0.5 | 96 | 99 | 98 | 2 | 5 |
|  | 0.25 | 101 | 100 | 99 | 3 | 6 |
| 10 | 1 | 78 | 99 | 105 | 0 | 7 |
|  | 0.5 | 85 | 107 | 110 | 0 | 8 |
|  | 0.25 | 92 | 104 | 109 | 1 | 9 |
| 16 | 1 | 88 | 100 | 103 | 0 | 10 |
|  | 0.5 | 95 | 102 | 104 | 2 | 11 |
|  | 0.25 | 102 | 99 | 100 | 3 | 12 |
| 29 | 1 | 79 | 98 | 109 | 0 | 13 |
|  | 0.5 | 86 | 102 | 108 | 0 | 14 |
|  | 0.25 | 94 | 106 | 104 | 1 | 15 |
| 30 | 1 | 82 | 99 | 108 | 0 | 16 |
|  | 0.5 | 87 | 97 | 105 | 0 | 17 |
|  | 0.25 | 96 | 106 | 103 | 2 | 18 |
| No treatment | — | 100 (80.5 cm) | 100 (18.7 cm) | 100 (3.41 g) | 3 |  |

TABLE 9

Length between nodes of rice

| Plot No. | $N_0$ | $N_1$ | $N_2$ | $N_3$ | $N_4$ |
|---|---|---|---|---|---|
| 1 | 94 | 46 | 86 | 91 | 97 |
| 2 | 98 | 56 | 95 | 96 | 100 |
| 4 | 97 | 55 | 97 | 90 | 98 |
| 7 | 93 | 43 | 83 | 86 | 98 |
| 10 | 97 | 57 | 96 | 94 | 102 |
| 13 | 92 | 43 | 91 | 85 | 100 |
| 16 | 93 | 47 | 95 | 93 | 96 |
| No treatment | 100 (3.45) | 100 (18.5) | 100 (13.7) | 100 (9.7) | 100 (3.8 cm) |

TEST EXAMPLE 8: Foliar treatment tests on trees

To a solution of an emulsifiable concentrate of Compound No. 10 having a predetermined concentration was applied to various trees grown in pots of 200 cm² and 400 cm² by means of a spray gun in an amount of 15 liter/a when new branches grew to a few cm after branches were trimmed. For spraying, the pot was placed in a box of 40 cm ×50 cm, and the mixture was uniformly sprayed in the box.

Three months later, the growth of the new branches were evaluated by the standards of Test Example 3. The results are shown in Table 10.

The height of the each tree at the time of spraying was as follows.

| | |
|---|---|
| Azelea (*Rhododendron indicum*): | 25–30 cm |
| Box tree (*Buxus microphylla*): | 20–25 cm |
| Chinese hawthorn (*Photinia glabra*): | 35–40 cm |
| Abelia (*Abelia serrata*): | 40–50 cm |
| Spindle tree (*Euonymus japonicus*): | 50–60 cm |
| Enkianthus perulatus: | 30–35 cm |
| Pomegranate (*Punica granatum*): | 30–40 cm |
| Juniperus chinensis: | 50–60 cm |

TABLE 10

Growth inhibition of new branches of trees Compound No. 10

| Trees | Concentration (%) of active ingredient | | |
|---|---|---|---|
| | 0.05 | 0.1 | 0.2 |
| Rhododendron indicum | 3.5 | 4.5 | 5 |
| Buxus microphylla | 2 | 4 | 4.5 |
| Photinia glabra | 3 | 4.5 | 5 |
| Abelia serrata | 3 | 4 | 5 |
| Euonymus jeponicus | 2 | 4 | 5 |
| Enkianthus perulatus | 3.5 | 4.5 | 5 |
| Punica granatum | 3 | 4 | 5 |
| Juniperus chinenesis | 0 | 2 | 4 |

TEST EXAMPLE 9: Foliar treatment test on radish

To examine the inhibition of flower stalk development of radish, a field of early maturing radish (*Raphanus sativus*) sown in spring and grown to immediately before flower stem development was divided into plots so that each plot contained 6 plants. The wettable powder and aqueous solution having a predetermined concentration, a nonionic surfactant was added so that the applied concentration would be 500 ppm, and the mixture was applied in an amount corresponding to 10 liter/a in the respective plots by means of a sprayer, and the micro-granule formulation were applied manually.

One month later, the evaluation on each plant was conducted in the same manner as in Test Example 3. The results are shown in Table 11. (The numerical value is an average of 6 plants, and is rounded off to two decimal places.)

TABLE 11

Inhibition of flower stalk development of radish

| Compound No. | Formulation type and content | Applied amount g/a Formulation | Active ingredient | Inhibition |
|---|---|---|---|---|
| 1 | Micro-granule formulation 1% | 500 | 5 | 4 |
| | | 250 | 2.5 | 3.2 |
| | | 125 | 1.25 | 1.5 |
| 5 | Wettable powder 50% | 10 | 5 | 4.7 |
| | | 5 | 2.5 | 3.3 |
| | | 2.5 | 1.25 | 2.2 |
| 11 | Emulsifiable concentrate 25% | 20 | 5 | 5 |
| | | 10 | 2.5 | 4.1 |
| | | 5 | 1.25 | 3.2 |
| 16 | Wettable powder 50% | 10 | 5 | 4.3 |
| | | 5 | 2.5 | 3.3 |
| | | 2.5 | 1.25 | 2.0 |
| 29 | Aqueous solution 100% | 5 | 5 | 4.7 |
| | | 2.5 | 2.5 | 3.5 |
| | | 1.25 | 1.25 | 2.7 |

TEST EXAMPLE 10: Non-agricultural field spraying test

To examine the growth inhibition of large weeds, a field of miscanthus (*Miscanthus sinensis*) and goldenlod (*Solidago altissima*) grown luxuriantly was divided into spray plots of 2.5×4 m. Diluted solutions of the wettable powder of Compound No. 1 (which contained 0.1% fixing agent) and the emulsifiable concentrate of Compound No. 10 were applied to the plots uniformly in an amount corresponding to 30 liter/a by means of a watering pot.

The average height and maximum height of miscanthus and goldenlod in the plots were measured at the time of the treatment and 3 months after the treatment.

The results are shown in Table 12.

TABLE 12

Growth inhibition of weeds in non-agricultural field

| Compound No. | g/are (A.I.) | Height of weeds (cm) | | | |
|---|---|---|---|---|---|
| | | Miscanthus | | Solidago | |
| | | At the treatment | 3 months later | At the treatment | 3 months later |
| 1 | 50 | 70–110 | 70–120 | 50–80 | 60–100 |
| | 25 | 60–100 | 80–140 | 50–70 | 70–120 |
| 10 | 50 | 70–110 | 80–120 | 60–80 | 60–110 |
| | 25 | 60–110 | 90–140 | 50–80 | 80–120 |
| No treatment plot | — | 60–110 | 170–220 | 50–70 | 150–190 |

TEST EXAMPLE 11: Thinning test on apples

Among branches of an apple tree (Fuji) of 25 years old, similar branches were selected, and 20 days after the full bloom, a solution of each compound having a predetermined concentration was sprayed over the entire branches by means of a sprayer in such amount that the solution sprayed was not dropped from the branches. Two months later, the fruit-bearing rate and the side to side diameter were examined. The results are shown in Table 13.

TABLE 13

Thinning test on apples

| Compound No. | Concentration (ppm) | Number of tested fruits | | Test results Ratio to no treatment (%) | | Average fruit diameter Ratio to non-treated branch (%) |
|---|---|---|---|---|---|---|
| | | | | Fruit bearing rate (%) | | |
| | | Center fruits | Side fruits | Center fruits | Side fruits | |
| 1 | 50 | 39 | 120 | 71.8 | 8.3 | 111 |
| | 25 | 32 | 101 | 87.5 | 9.9 | 114 |
| | 12.5 | 37 | 113 | 86.5 | 11.5 | 109 |
| 11 | 50 | 35 | 108 | 71.4 | 7.4 | 106 |
| | 25 | 37 | 110 | 86.5 | 10.0 | 112 |
| | 12.5 | 30 | 99 | 90.0 | 12.1 | 110 |
| Non Treated plot | — | 34 | 102 | 82.4 | 27.5 | 100 (35.9 mm) |

TEST EXAMPLE 12: Foliar treatment test on sugar cane

A field of sugar cane grown to the initial stage of ripening, was divided into plots so that each plot contained 5 plants, and 30 ml of a solution having a predetermined concentration of an active ingredient was applied by a hand sprayer to the base portion of the top leaves of each stem.

Two months later i.e. at the time of harvesting, some heading was observed in the non-treated plot, whereas no heading was observed in each of the treated plots. The plants were harvested and squeezed, and the sugar content of the pressed juice was measured by means of a polarimetric sugar content meter. The results are shown in Table 14.

TABLE 14

Results of measurement of sugar content of sugar cane

| Compound No. | Active ingredient (%) | Mean of sugar content (%) |
|---|---|---|
| 1 | 0.2 | 13.83 |

TABLE 14-continued
Results of measurement of sugar content of sugar cane

| Compound No. | Active ingredient (%) | Mean of sugar content (%) |
| --- | --- | --- |
| | 0.1 | 13.57 |
| 10 | 0.2 | 14.21 |
| | 0.1 | 13.84 |
| 29 | 0.2 | 12.98 |
| | 0.1 | 11.95 |
| Non-treated plot | — | 10.39 |

TEST EXAMPLE 13: Foliar treatment test on soybean

In a green house, soybean (Enrei) was grown in a 200 cm² pot (1 plant/pot). At the beginning of the 3 leaf stage, each compound diluted to a predetermined concentration and having 500 ppm of a nonionic surfactant added, was applied in an amount corresponding to 10 liter/a. The test was conducted with 3 plants per plot. Two months later, the number of pods formed were examined. The results are shown in Table 15. (The numerical value is an average of 3 plants, and is rounded off to two decimal places.)

TABLE 15

| Compound No. | Active ingredient (ppm) | Number of pods |
| --- | --- | --- |
| 1 | 30 | 31.0 |
| | 100 | 35.3 |
| | 300 | 33.3 |
| 11 | 30 | 28.3 |
| | 100 | 39.7 |
| | 300 | 38.0 |
| 29 | 30 | 25.0 |
| | 100 | 35.3 |
| | 300 | 37.3 |
| 30 | 30 | 26.0 |
| | 100 | 36.3 |
| | 300 | 32.7 |
| Non-treated plot | — | 24.7 |

We claim:

1. A benzamide derivative of the formula:

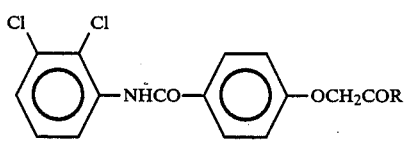   (I)

wherein R is hydroxyl, alkoxy, alkoxyalkoxy, alkoxyalkoxyalkoxy, alkenylalkoxy, alkenylalkoxyalkoxy, alkynylalkoxy, alkynylalkoxyalkoxy, monoalkylamino, dialkylamino or O-cat wherein cat is an inorganic or organic cation.

2. The benzamide derivative according to claim 1, which is selected from the group consisting of

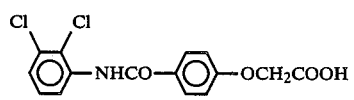

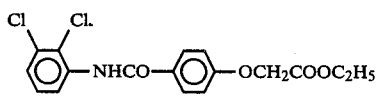

-continued

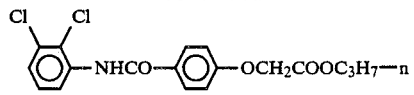

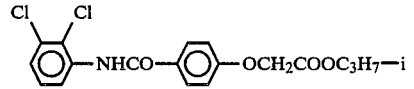

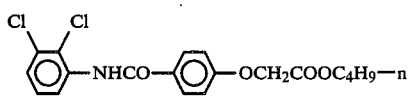

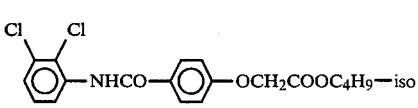

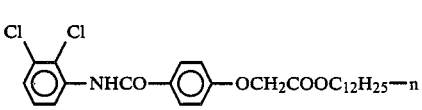

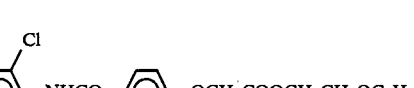

—OCH₂COOCH₂CH₂OCH₂CH₂OC₄H₉—n

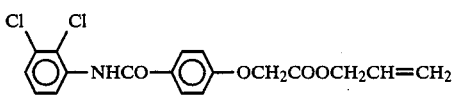

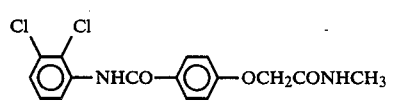

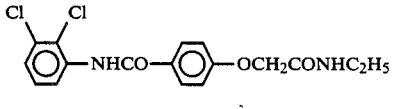

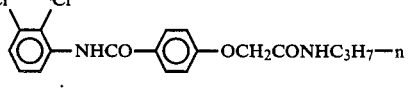

-continued
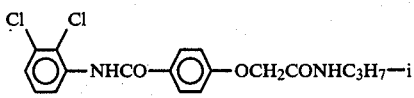
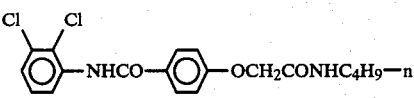
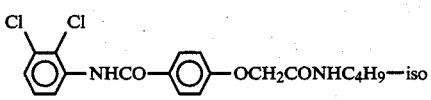
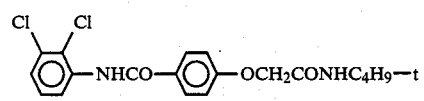
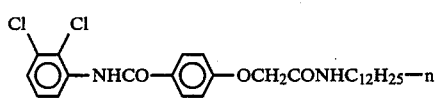
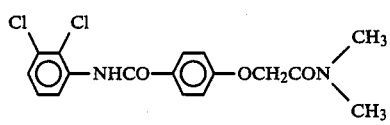
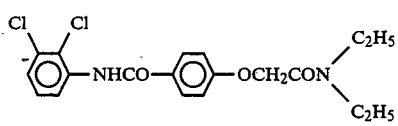
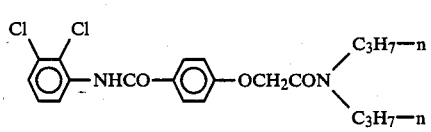
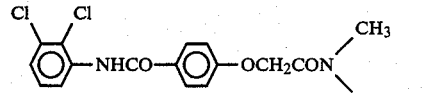
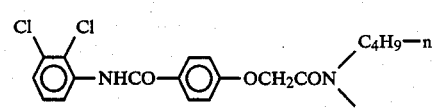
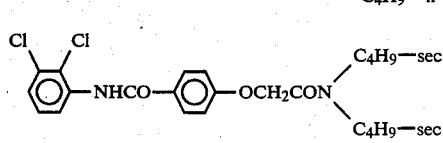
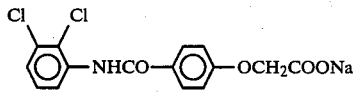
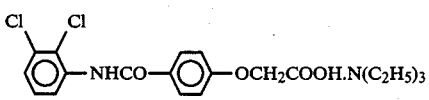
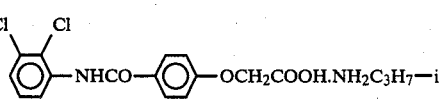
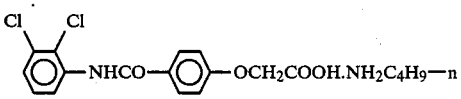
3. A plant growth regulant comprising an effective amount of a benzamide derivative of the formula I as defined in claim 1 and a carrier.
4. A method comprising applying to a plant a benzamide derivative of the formula I as defined in claim 1 in an amount effective as a plant growth regulant.
* * * * *